(12) United States Patent
Hauschildt et al.

(10) Patent No.: US 9,700,466 B2
(45) Date of Patent: Jul. 11, 2017

(54) HYGIENE ARTICLE CLOSURE TAB

(75) Inventors: Volker Hauschildt, Hilden (DE); Ralf G. Oertel, Neuss (DE); Peter Kitzer, Echt (NL)

(73) Assignee: 3M Innovative Properties Comany, St Paul, MN (US)

( * ) Notice: Subject to any disclaimer, the term of this patent is extended or adjusted under 35 U.S.C. 154(b) by 0 days.

(21) Appl. No.: 13/704,171

(22) PCT Filed: Jun. 15, 2011

(86) PCT No.: PCT/US2011/040415
§ 371 (c)(1),
(2), (4) Date: Dec. 13, 2012

(87) PCT Pub. No.: WO2011/163020
PCT Pub. Date: Dec. 29, 2011

(65) Prior Publication Data
US 2013/0095279 A1    Apr. 18, 2013

(30) Foreign Application Priority Data

Jun. 21, 2010 (EP) .................................... 10166719

(51) Int. Cl.
*A61F 13/62* (2006.01)
*A61F 13/56* (2006.01)

(52) U.S. Cl.
CPC ........ *A61F 13/622* (2013.01); *A61F 13/5611* (2013.01); *A61F 13/5616* (2013.01);
(Continued)

(58) Field of Classification Search
CPC . A61F 13/622; A61F 13/5616; A61F 13/5611
(Continued)

(56) References Cited

U.S. PATENT DOCUMENTS 3,020,613 A  *  2/1962  Morin ............................. 24/452
4,568,344 A     2/1986  Suzuki et al.
(Continued)

FOREIGN PATENT DOCUMENTS

EP         0755665 A1     1/1997
EP         0941730 A1     9/1999
(Continued)

*Primary Examiner* — David Sample
*Assistant Examiner* — Donald M Flores, Jr.

(57) ABSTRACT

A hygiene article closure tab, for use with a hygiene article such as a diaper, adult incontinence articles or feminine hygiene articles, is disclosed. The closure tab comprises a backing layer having a region adapted to carry at least one mechanical fastening means and a region adapted to form a fingerlift portion, the fingerlift portion being free from any fastening means. A first mechanical fastening means is carried on the backing layer adjacent the fingerlift portion, and has a width $w_1$. A second mechanical fastening means is carried on the backing layer, and has a width $w_2$ and is separated from the first mechanical fastening means by a separation distance $d_1$. The width $w_1$ of the first mechanical fastening means is greater than the separation distance $d_1$, and the width $w_2$ of the second mechanical fastening means is greater than the width $w_1$ of the first mechanical fastening means.

15 Claims, 4 Drawing Sheets

(52) U.S. Cl.
CPC .......... *A61F 13/5622* (2013.01); *A61F 13/62* (2013.01); *Y10T 428/24008* (2015.01)

(58) Field of Classification Search
USPC .......................................... 24/444
See application file for complete search history.

(56) References Cited

U.S. PATENT DOCUMENTS

| | | | |
|---|---|---|---|
| 4,753,648 A * | 6/1988 | Jackson | 604/389 |
| 5,321,855 A * | 6/1994 | Ciuffo | 2/239 |
| 5,851,205 A * | 12/1998 | Hisada et al. | 604/390 |
| 5,997,522 A * | 12/1999 | Provost et al. | 604/391 |
| 6,030,373 A * | 2/2000 | VanGompel et al. | 604/386 |
| 7,125,400 B2 | 10/2006 | Igaue et al. | |
| 2004/0022998 A1 | 2/2004 | Miyamoto et al. | |
| 2005/0043700 A1* | 2/2005 | Otsubo et al. | 604/387 |

FOREIGN PATENT DOCUMENTS

| | | |
|---|---|---|
| EP | 1663095 B1 | 10/2008 |
| JP | 63-21903 | 1/1988 |
| JP | 10-28703 | 2/1998 |
| JP | 2008-161571 | 7/2008 |

\* cited by examiner

HYGIENE ARTICLE CLOSURE TAB

FIELD OF THE INVENTION

The present invention relates to a hygiene article closure tab, in particular, a closure tab employing mechanical fastening means.

BACKGROUND

Hygiene articles, particularly disposable hygiene articles have a variety of uses, including infant diapers (sometimes also known as nappies), feminine hygiene articles (such as sanitary towels or napkins and panty liners), and adult incontinence wear (for example, incontinence pads and disposable undergarments). Each of these articles is designed to absorb and/or retain liquids and other body exudates and has in common the need for the article to be fixed in position relative to the body of a wearer. This may be done by adhering the article directly to itself such that it surrounds a wearer (in the case of infant diapers and disposable undergarments) or to an item of clothing (in the case of feminine hygiene articles and adult incontinence pads), or directly to the skin of a user (in the case of feminine hygiene articles and incontinence pads).

In the case of hygiene articles such as diapers and disposable undergarments, closure tabs are often provided in order to enable the article to adhere directly to itself. The closure tab typically comprises an elongate strip of non-woven material divided into a user end and a manufacturer end. Alternatively, the closure tab may form part of an ear panel of an article, such as a diaper, which is an extended portion of one of the front portion or the rear portion of the hygiene article, and therefore typically has only a user end, as the manufacturer end is integral with the ear panel. The user end is provided with a fingerlift portion, typically comprising a fastening-free region, to enable a user to grab hold of the closure tab between thumb and forefinger such that the tab can be closed (meshed with or adhered firmly to a surface of the hygiene article) and opened (released from a surface of the hygiene article). At least one region of the user end may be provided with an adhesive and/or mechanical fastening means. The manufacturer end of the closure tab is again a fastening-free region, and is provided to allow the closure tab to be fixed firmly to the hygiene article. This may be by means of an adhesive, or a thermal or ultrasonic welding process. The non-woven material may be reinforced along part or all of the length of the closure tab, and the fingerlift portion may be shaped, for example, by providing a scalloped edge, to make lifting the user end of the closure tab up from the surface of the hygiene article easier for the user.

One particular situation where the fingerlift portion provides advantages for a user of a hygiene article is during the opening or removal of the closure tab from a surface of the hygiene article. For example, if a mechanical fastening means is employed to fasten the closure tab to the hygiene article, the elements of the mechanical fastening means (such as hooks, stems or cup-like protrusions) will mesh with the fibres of the region of the hygiene article used as a landing zone. In order to open the closure tab, the user must provide a certain level of force to unmesh the fastening elements from the fibres of the landing zone. For a particular width of mechanical fastening means provided on a closure tab, having a leading edge adjacent the fingerlift portion, and a trailing edge adjacent the manufacturer end, the force required to remove it increases steadily from an initial value require to release the leading edge until the trailing edge is finally free. A user therefore experiences an increased resistance to pulling whilst the closure tab is being removed, and a sudden decrease when the trailing edge is finally free. This means that a user may feel that the closure tab was not adequately secured in the first place.

One method of reducing this user perception of difficulty in removal or inadequate security is to divide the mechanical fastening means into several regions extending across the width of the closure tab, and along the length of the user end. One example of this is discussed in U.S. Pat. No. 6,030,373. A fastening tab includes a user bond portion having a leading and a trailing edge separated from each other by a lateral spacing distance, and has a securing mechanism (such as a mechanical fastening means) at each of the leading and trailing edges. The lateral spacing distance helps to distribute closure stresses more evenly. A similar effect is described in EP 1 663 095 B1, where a hook fastening material is provided on the surface of an ear panel provided on a diaper. The hook material is divided into two regions, separated by a gap. It is suggested that the gap reduces the transmission of the induced stress developed in one of the fastening materials to the other, which in turn reduces the likelihood that one of the fastening materials can become detached due to this stress. Similarly, EP 0 755 665 A1 discusses the use of two regions of hook and loop fastening material rather than a single region, as this reduces the chance of the fastening becoming unintentionally disengaged.

Each of these documents deals with the issue of the perception of the user that the closure tab may not be securely fastened. However, there is still the issue of how a user perceives the force required to open or release the closure tab, and whether this has a negative impact on how well the user feels the hygiene article is secured, as well as the issue of the ease with which a well-secured closure tab can be removed completely from a landing zone.

SUMMARY

The present invention aims to address these problems by providing a hygiene article closure tab, comprising: a backing layer having a region adapted to carry at least one mechanical fastening means and a region adapted to form a fingerlift portion, the fingerlift portion being free from any fastening means; a first mechanical fastening means carried on the backing layer adjacent the fingerlift portion, and having a width $w_1$; and a second mechanical fastening means carried on the backing layer, having a width $w_2$ and separated from the first mechanical fastening means by a separation distance $d_1$; wherein the width $w_1$ of the first mechanical fastening means is greater than the separation distance $d_1$ and the width $w_2$ of the second mechanical fastening means is greater than the width $w_1$ of the first mechanical fastening means.

By using two regions of a mechanical fastening means, separated from each other by a small separation distance (where small indicates that the separation distance is smaller than the width of the first mechanical fastening means) the user experiences a resistance when attempting to remove or open the hygiene article closure tab, indicating that it is fastened securely. In addition, by providing two regions of mechanical fastening means the user perceives that the tab is easier to open as there is no sudden jerk when the fastening means are finally released from a landing zone material. Providing asymmetric regions of mechanical fastening means has a beneficial effect on the perception of both a maximum peel force and the separation of peel and shear forces, giving the user a perception of ease of removal and secure fastening.

Preferably, the first and second mechanical fastening means comprise hook, stem or cup-shaped mechanical fastening elements. Preferably the first and second mechanical fastening means are adapted to engage with one of fluffy non-woven material, extrusion-bonded loop material, knitted loop material and hook to backsheet material. Such mechanical fastening elements and landing zone materials are particularly suitable for use with hygiene articles.

The first mechanical fastening means may comprise mechanical fastening elements optimised to resist peel force and the second mechanical fastening means may comprise mechanical fastening elements optimised to resist shear force. By optimising the properties of the fastening elements of the mechanical fastening means, the overall experience of the user can also be optimised.

The sum of the widths $w_1$ of the first mechanical fastening means and $w_2$ of the second mechanical fastening means is preferably in the range 7 to 22 mm. The separation distance $d_1$ is preferably in the range 0.5 to 1.0 mm. Such ranges are particularly beneficial in creating the desired feel and response of the hygiene article closure tab experienced by a user.

The hygiene article closure tab may further comprise a third mechanical fastening means carried on the backing layer, having a width $w_3$ and separated from the second mechanical fastening means by a separation distance $d_2$. Increasing the number of regions of mechanical fastening means can be used to enhance both the initial peel force and the ease with which a user is able to open or remove the hygiene article closure tab. Preferably, the width $w_3$ of the third mechanical fastening means is equal to the width $w_2$ of the second mechanical fastening means. Alternatively, the width $w_3$ of the third mechanical fastening means is not equal to the width $w_2$ of the second mechanical fastening means. The separation distance $d_1$ between the first and second mechanical fastening means may be equal to the separation distance $d_2$ between the second and third mechanical fastening means. A fourth mechanical fastening means carried on the backing layer, having a width $w_4$ and separated from the second mechanical fastening means by a separation distance $d_3$ may also be provided. These options give overall flexibility in the design of the hygiene article closure tab whilst still ensuring the user has the perception of a securely fastened hygiene article closure tab that is easy to remove or open.

The backing layer may comprise a non-woven material layer and an adhesive layer. This construction is particularly suitable for hygiene articles where the tab is formed separately to the article itself, for example, infant diapers. Alternatively, the backing layer may be formed by the backsheet material of a hygiene article. By utilising the backsheet material to form a hygiene article closure tab, it is possible to apply the invention as a closure tab for a hygiene article where the closure mechanism is typically formed as part of the article, for example some diaper designs or feminine hygiene articles.

DETAILED DESCRIPTION OF THE DRAWINGS

The present invention will now be described by way of example only, and with reference to the accompanying drawings, in which.

In the present invention it has been realised that by carefully choosing the widths of the mechanical fastening means provided on a hygiene article closure tab, not only can the risk of one fastening means becoming released inadvertently, that is, the user's perception of how well secured the closure tab is to the hygiene article, be reduced, but also the user's perception of the amount of force required to open or release the closure tab can be altered. A hygiene article closure tab in accordance with the first and second embodiments of the present invention is particularly suitable for use with hygiene articles such as infant diapers and disposable undergarments, particularly those having an incontinence pad function. Although in each of these embodiments, the closure tab is described in terms of an elongate strip, it will be obvious to one skilled in the art that each embodiment may be used in connection with a hygiene article having an ear panel portion where no elongate strip is attached, but where the mechanical fastening means are mounted directly onto the ear panel itself. This is similar to the third embodiment of the present invention, which is particularly suited (but not limited to) for use with a feminine hygiene article comprising wing portions or a diaper having ear panels on which mechanical fastening means are fixed, and hence the hygiene article closure tab is integral with the hygiene article. A fourth embodiment of the present invention is particularly suitable where a hygiene article is not provided with wing or other similar portions, and the hygiene article closure tab is effectively integral with the backsheet material of the hygiene article, for example, a feminine hygiene article such as a panty liner.

Figure 1:
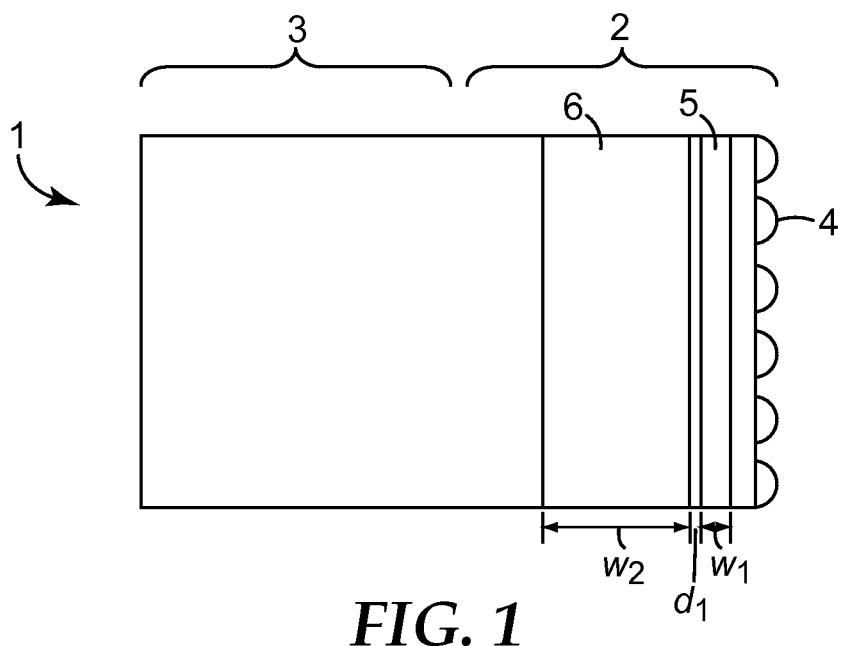
FIG. 1 is a schematic view of the positioning of the mechanical fastening means on a hygiene article closure tab in accordance with a first embodiment of the present invention.

FIG. 1 is a schematic view of the positioning of the mechanical fastening means on a hygiene article closure tab in accordance with a first embodiment of the present invention. The view is of the underside of the hygiene article closure tab, showing the mechanical fastening means. The hygiene article closure tab 1 is in the form of an elongate strip, having two opposing long sides and two opposing short sides, formed from a backing layer supporting a layer of a non-woven material (not shown). The hygiene article closure tab 1 is provided with a user end 2 and a manufacturer end 3. The user end 2 comprises a fingerlift portion 4, having a scalloped edge, a first mechanical fastening means 5 carried on the backing layer, and a second mechanical fastening means 6, also carried on the backing layer. Each of the first 5 and second 6 mechanical fastening means extends across the width of the hygiene article closure tab, and has edges parallel with the opposing short sides of the elongate strip. The first mechanical fastening means 5 has a width $w_1$, and the second mechanical fastening means 6 has a width $w_2$, where the width $w_2$ of the second mechanical fastening means 6 is greater than the width $w_1$ of the first mechanical fastening means. The first 5 and second 6 mechanical fastening means are separated by a separation distance $d_1$. In this embodiment, the width $w_1$ of the first fastening means 5 is greater than the separation distance $d_1$. By minimising the separation distance $d_1$ the percentage surface area without any mechanical fastening means is minimised, but the effect of providing two separate mechanical fastening means is maintained. The widths of the mechanical fastening means and the separation distance may be optimised as described in further detail below.

Figure 2:
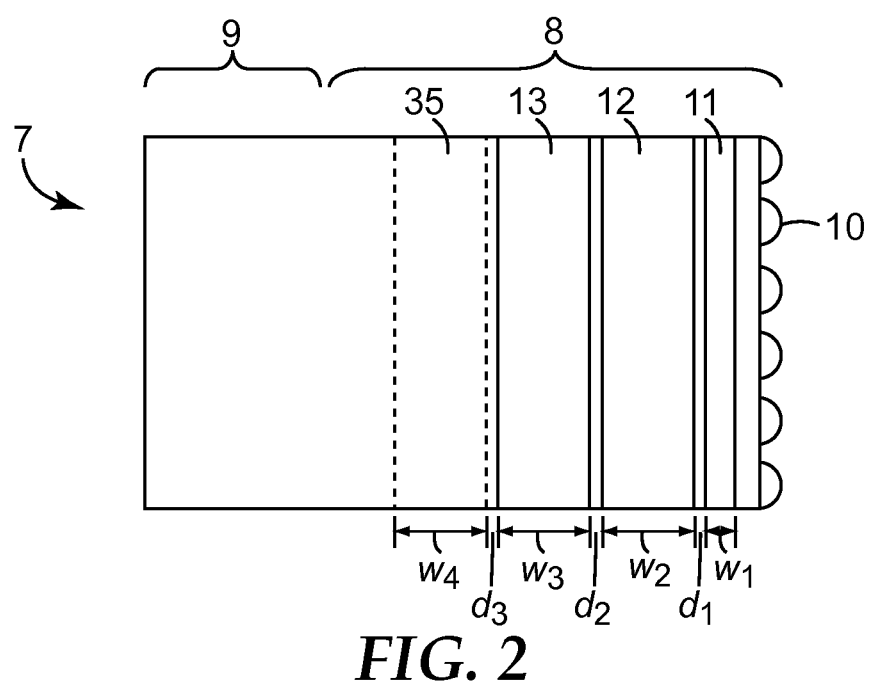
FIG. 2 is a schematic view of the positioning of the mechanical fastening means on a hygiene article closure tab in accordance with a second embodiment of the present invention.

FIG. 2 is a schematic view of the positioning of the mechanical fastening means on a hygiene article closure tab in accordance with a second embodiment of the present invention. The view is of the underside of the hygiene article closure tab, showing the mechanical fastening means. The hygiene article closure tab 7 is in the form of an elongate strip, having two opposing long sides and two opposing short sides, formed from a backing layer supporting a layer of a non-woven material (not shown). The hygiene article closure tab 7 is provided with a user end 8 and a manufacturer end 9. The user end 8 comprises a fingerlift portion 10, having a scalloped edge, a first mechanical fastening means 11 carried on the backing layer, a second mechanical fastening means 12, also carried on the backing layer and a third fastening means 13, again also carried on the backing layer. Each of the first 11, second 12 and third 13 mechanical fastening means extends across the width of the hygiene article closure tab, and has edges parallel with the opposing short sides of the elongate strip. The first mechanical fastening means 11 has a width $w_1$, and the second mechanical fastening means 12 has a width $w_2$, where the width $w_2$ of the second mechanical fastening means 12 is greater than the width $w_1$ of the first mechanical fastening means. The third mechanical fastening means 13 has a width $w_3$, where the width of the third fastening means $w_3$ is greater than the width $w_1$ of the first fastening means 11, but, in this embodiment, equal to the width $w_2$ of the second fastening means 12. Again, the first 11 and second 12 mechanical fastening means are separated by a separation distance $d_1$, and in this embodiment, the second mechanical fastening means 12 are separated from the third mechanical fastening means 13 by a separation distance $d_2$. The width $w_1$ of the first fastening means 11 and the width $w_2$ of the second fastening means 12 and the width $w_3$ of the third fastening means 13 are greater than the separation distance $d_1$, and are greater than the separation distance $d_2$. The two separation distances, $d_1$ and $d_2$ are substantially equal to each other. The width $w_3$ of the third mechanical fastening means is substantially equal to the width $w_2$ of the second mechanical fastening means in this embodiment, but may be chosen to be narrower or wider depending on the landing zone material and mechanical fastening means chosen. Again, the width of the mechanical fastening means and the second separation distance may be optimised, as described below. A fourth mechanical fastening means 35 having a width $w_4$, separated from the third mechanical fastening means 13 by a separation distance $d_3$ can also be included. The two separation distances, $d_2$ and $d_3$ are substantially equal to each other. The width $w_4$ of the fourth mechanical fastening means 35 is substantially equal to the width $w_3$ of the third mechanical fastening means 13 in this embodiment, but may be chosen to be narrower or wider depending on the landing zone material and mechanical fastening means chosen. Again, the width of the mechanical fastening means and the second separation distance may be optimised, as described below.

Figure 3:
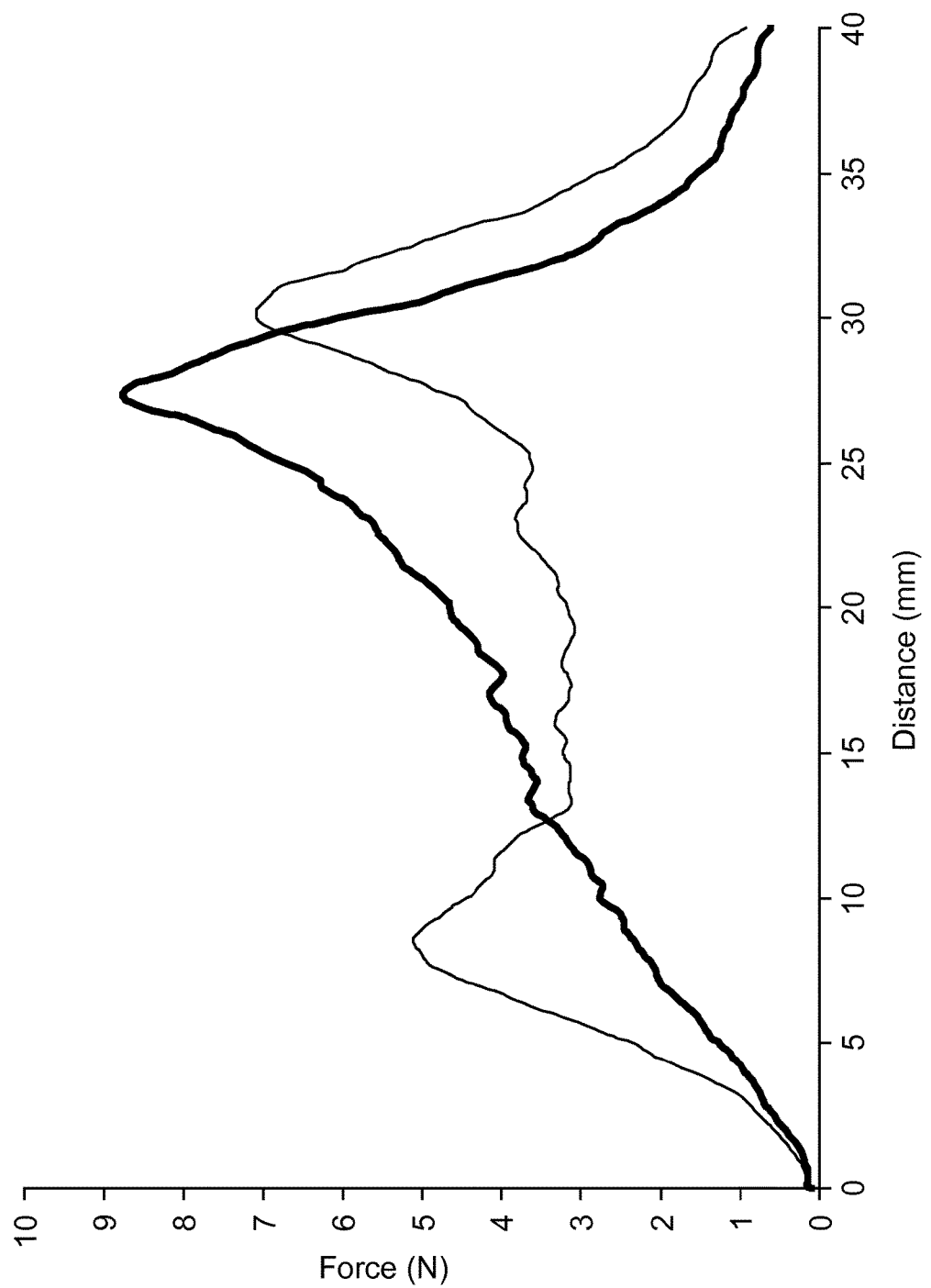
FIG. 3 is a chart showing peel force required to open or release a hygiene article closure tab in accordance with a first embodiment of the present invention compared with a conventional hygiene article closure tab.

FIG. 3 is a chart showing peel force required to open or release a hygiene article closure tab in accordance with a first embodiment of the present invention (faint line) compared with a conventional hygiene article closure tab (solid line). The chart shows force (in N) along the y-axis, and the width of the mechanical fastening means removed from a backing material (shown as distance in mm) along the x-axis. A hygiene article closure tab in accordance with a first embodiment of the present invention was formed by providing two mechanical fastening means comprising CHK-02220 hooks (available from 3M Company, 3M Center, St. Paul, Minn. 55144-1000, USA) adhered to an adhesive-coated non-woven backing layer. A coverlayer is provided on the user end of the hygiene article closure tab to create a fingerlift portion. The first fastening means is positioned adjacent the fingerlift portion, and has a width $w_1$ of 3 mm, and is separated from a second mechanical fastening means having a width $w_2$ of 10 mm by a separation distance $d_1$ of 0.5 mm. The conventional hygiene article closure strip was of the same basic construction, but with a single mechanical fastening means having a width of 13 mm. Each hygiene article closure tab was placed on a landing zone formed from an extrusion bonded loop material (EBL-Soft, available from 3M Company, 3M Center, St. Paul, Minn. 55144-1000, USA), and subjected to a 180° peel force in a tensile tester. Initially, the sample was pressed onto the lading zone material using a 2 kg weight rolled across the surface, and the sample loaded with a 1 kg weight hung vertically for 10 seconds. Both ends of the sample were then placed in a tensile tester, producing a T-peel mode 180° peel test. The peel force test was repeated 8 times, and an average taken to create the curves shown in FIG. 3.

FIG. 3 illustrates that for the conventional hygiene article closure tab a substantially constant increase in peel force is required as the mechanical fastening means is removed from a landing zone. This gives an impression to a user of the hygiene article closure tab that it is difficult to remove, and as increasing force is required until completely released, there is an unpleasant sensation as the hygiene article closure tab is suddenly pulled free from the landing zone, as the user is unaware of at what point the increasing force no longer needs to be applied. Conversely, the user may also gain the impression that hygiene article closure tab is not necessarily fastened securely, as the initial force required to remove the hygiene article closure tab is relatively low.

FIG. 3 also illustrates that for a hygiene article closure tab in accordance with a first embodiment, the amount of peel force required is effectively in two stages: a first stage having a greater rate of increase in peel force when compared with the conventional hygiene article closure tab, and a second stage having lower rate of increase in peel force compared with the first region. These two regions are separated by a drop in peel force accounted for by the separation distance between the first and second mechanical fastening means. By having a greater rate of increase in peel force experienced initially over a short peel distance, the user feels immediately that the hygiene article closure tab is securely fastened, as it requires a substantial applied force to begin the opening process. By ensuring that there is a drop in the peel force followed by a lower rate of increase in peel force until the hygiene article closure tab is removed, the user does not experience the same sudden release associated with the conventional hygiene article closure tab, mainly due to the fact that as it is perceived that the hygiene article closure tab is firmly closed or affixed to the landing zone. This is achieved by ensuring that the width $w_1$ of the first mechanical fastening means is greater than the separation distance $d_1$ and that the width $w_2$ of the second mechanical fastening means is greater than the width $w_1$ of the first mechanical fastening means.

Without wishing to be bound by any particular theory, it is likely that the provision of two mechanical fastening means having different widths, and separated by a separation distance, results in there being two different types of force being provided by the user to open the hygiene article closure tab. Initially, the user needs to provide a peel force, that is, a force in a direction approximately perpendicular to the plane of the hygiene article closure tab when in contact with the landing zone. This perpendicular force causes the mechanical fastening elements at the leading edge of the first mechanical fastening means to disengage with the material of the landing zone. As the width $w_1$ of the first mechanical fastening means is relatively small compared with the overall width between the leading and trailing edges of the hygiene article closure tab, virtually all of the first mechanical fastening means will be removed by applying a perpendicular force. At the point that the entire first mechanical fastening means is removed from the landing zone, a drop in applied force is experienced at the separation distance between the first and second mechanical fastening means. Although a small perpendicular force is required initially to release the first row of mechanical fastening elements of the second mechanical fastening means, the majority of the force is naturally applied by the user in a direction parallel to the plane of the hygiene article closure tab when in contact with the landing zone, that is, a shear force. In the conventional hygiene article closure tab a perpendicular peel force is applied in order to release the mechanical fastening elements from the landing zone material initially, followed by a parallel shear force. There is no clear distinction between the need for a peel force and the need for a subsequent shear force, which results in the user simultaneously trying to rip the hygiene article closure tab off the landing zone by a combination of perpendicular and parallel forces. This creates the impression that the hygiene article closure tab becomes increasingly difficult to remove or open, yet may not be fastened or closed securely.

The role of the separation distance between the first and second mechanical fastening means is also key to providing the user with the impression that the hygiene article closure tab is securely fastened or closed, but yet is easy to open or remove. Initially, as the perpendicular force is applied, the user builds up momentum in the opening process, which naturally ceases at the point the first mechanical fastening means is fully released from the landing zone. However, in order not to lose this momentum completely, it is important that the separation distance is not too great, such that the first row of mechanical fastening elements of the second mechanical fastening means is easily disengaged from the material of the landing zone by the same perpendicularly applied force. This then ensures a smooth transition to the parallel shear force, releasing the remainder of the second mechanical fastening means from the material of the landing zone. If the separation distance is too large, the drop in applied peel force between the first and second peaks shown in FIG. 3 for the hygiene article closure tab in accordance with the first embodiment of the present invention would be greater, giving a perception to the user that the second mechanical fastening means would require some sort of tugging motion to release it from the surface of the landing zone. If the separation distance is too small, the user experiences a similar rate of increase of required force as for a conventional hygiene article closure tab, with its associated perceptions in use. An experimental determination of the preferred range of separation distance shows this to be between 0.5 mm to 1.0 mm.

Figure 4:
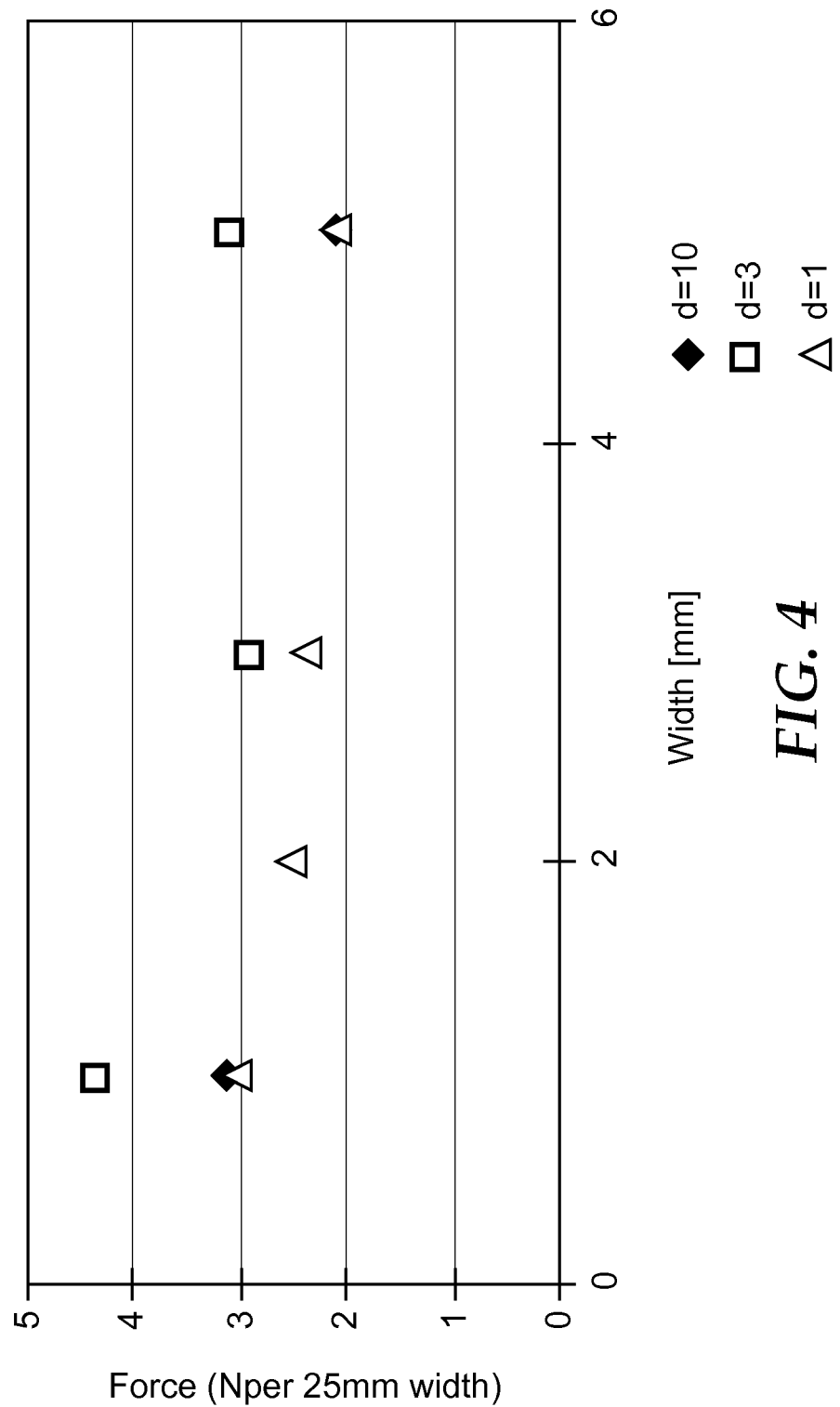
FIG. 4 is a chart showing peak peel force required to open or release a hygiene article closure tab for different widths of mechanical fastening means, and different separation distances.

This preferred range is further illustrated by the data shown in FIG. 4. FIG. 4 is a chart showing peak peel force required to open or release a hygiene article closure tab for different widths of mechanical fastening means, and different separation distances. A 25 mm wide test-strip, comprising a laminated backing material (a layer of 42 $g/m^2$ spunbound non-woven material and a layer of 20 $g/m^2$ polypropylene/polyethylene co-polymer) and carrying polypropylene hooks (having a base weight of 100 $g/m^2$) attached to the backing material using an adhesive tape, was subjected to a 90° peel test. Initially, samples were placed on a knitted loop landing zone attached to a metal base plate, again using adhesive tape, and rolled using a 2 kg roller press to achieve meshing between the hooks and loop material. A shear treatment comprising a horizontal pull force provided by a 1 kg weight for 2 seconds was carried out, followed by a pull speed of 300 mm/min peel test to remove the testing strips from the knitted loop landing zone. A total fastening region width of approximately 20 mm for each test sample was created using a combination of hook regions and separation distances. The following values of widths and separation distances were used:

width of mechanical fastening means, w: 1 mm, 3 mm, 10 mm separation distance, d: 1 mm, 2 mm, 3 mm, 4 mm, 5 mm Samples combining each width w and each separation distance d were measured. The peak force required to peel the samples from a loop material (in terms of N per 25 mm width) was recorded. From these results the optimum value of the separation distance d is 1 mm, with the peak force reducing as the separation distance increases for each width w of mechanical fastening means.

In addition, in order to be able to replace a conventional hygiene article closure tab with ease, it is preferred that the sum of the widths $w_1$ of the first mechanical fastening means and $w_2$ of the second mechanical fastening means is in the range 7 to 22 mm. A preferred range of widths $w_1$ of the first mechanical fastening means is between 1.0 mm and 5.0 mm, and for widths $w_2$ of the second mechanical fastening means is between 5.0 mm and 18.0 mm.

Preferably, the first and second mechanical fastening means comprise one of hook, stem or cup-shaped mechanical fastening elements. It is not necessary for both first and second mechanical fastening means to have the same mechanical fastening elements. For example, as a result of the considerations of the different types of force applied to the hygiene article closure tab described above, the first mechanical fastening means may comprises mechanical fastening elements optimised to resist peel force, and the second mechanical fastening means may comprise mechanical fastening elements optimised to resist shear force. This may be achieved by choosing a specific shape for the mechanical fastening elements, or by optimising the material used to form the mechanical fastening elements. The landing zone may be formed from a material such as fluffy non-woven material, extrusion-bonded loop material, knitted loop material and hook to backsheet material, with the mechanical fastening means being adapted to engage with the chosen material. A suitable backing layer for the hygiene article closure tab comprises a non-woven material layer and an adhesive layer. This may be, for example, a non-woven tape material having an adhesive layer on one surface. Alternatively, the backing layer may be tape based on a thermoplastic film, such as a polypropylene film or a film comprising a blend or polypropylene and polyethylene (PP and PE) materials.

In the above two embodiments of the present invention, the hygiene article closure tab is designed for use as a tab affixed to a hygiene article such as a diaper, either directly to the backsheet of the diaper, or to ear panels provided by extensions to the backsheet and frontsheet materials. However, in the third embodiment of the present invention it is envisaged that the use of first and second mechanical fastening means having different widths, and separated by a separation distance, may be applied to other hygiene articles, such as sanitary towels that comprise wing portions, and to diapers with ear panels, where a separate closure tab is not provided. In each of these situations the hygiene article closure tab is integral with the hygiene article itself.

Figure 5:
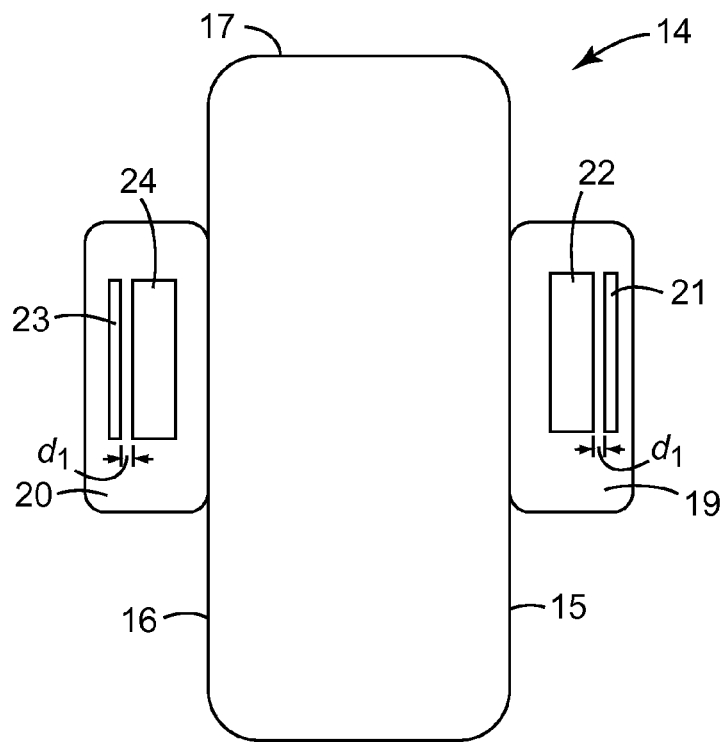
FIG. 5 is a schematic view of the positioning of the mechanical fastening means on a hygiene article closure tab in accordance with a third embodiment of the present invention.

FIG. 5 is a schematic view of the positioning of the mechanical fastening means on a hygiene article closure tab in accordance with a third embodiment of the present invention. This shows a view of a feminine hygiene article such as a sanitary towel having wing portions with the backsheet uppermost, but the embodiment may just as easily be applied to the ear panels of a diaper. A sanitary towel 14, generally elongate in shape having opposing longitudinal sides 15, 16, and opposing transverse sides 17, 18, is provided with first 19 and second 20 wing portions, each one located approximately halfway along a respective opposing longitudinal side 15, 16. Each wing portion 19, 20 is formed from an extension of the frontsheet and backsheet materials, with an absorbent core (not shown) being provided between the frontsheet and backsheet in a central region of the sanitary towel 14. Each of the first 19 and second 20 wing portions is provided with a first 21, 23 and second 22, 24 mechanical fastening means, the first 21, 23 mechanical fastening means having a width $w_1$ and the second mechanical fastening means 22, 24 having a width $w_2$, and being separated by a separation distance $d_1$. In all other respects, the first 21, 23 and second 22, 24 mechanical fastening means and the separation distances $d_1$ are the same as described with respect to the first and second embodiments of the present invention described above. In this example, each wing portion 19, 20 may be secured firmly to the underside of the gusset of a wearer's underwear by means of the mechanical fastening means. However, it may be desirable that only one of the wing portions 19, 20 is provided with mechanical fastening means, and the frontsheet material of the other wing is used as a landing zone, with the wings overlapping and engaging to secure the sanitary towel in use.

Figure 6:
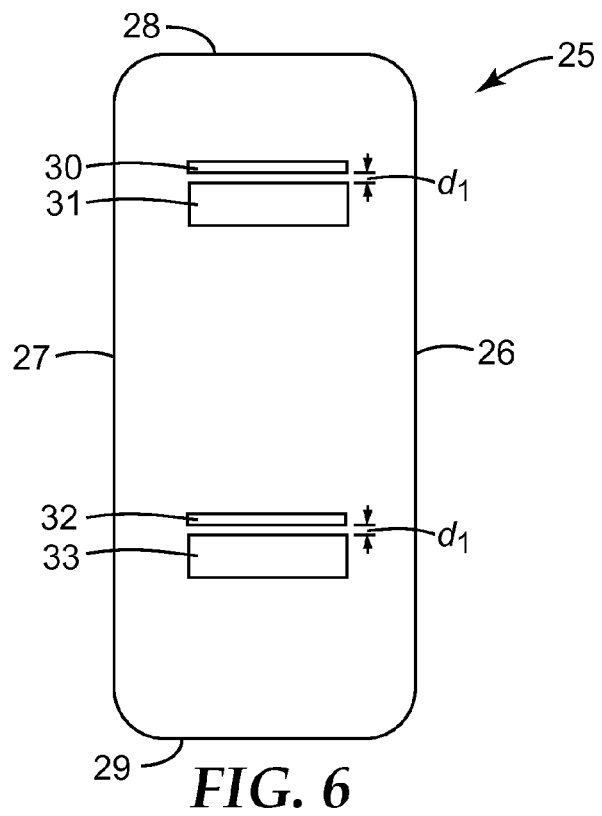
FIG. 6 is a schematic view of the positioning of the mechanical fastening means on a hygiene article closure tab in accordance with a fourth embodiment of the present invention.

FIG. 6 is a schematic view of the positioning of the mechanical fastening means on a hygiene article in accordance with a fourth embodiment of the present invention. This shows a view of a feminine hygiene article such as a sanitary towel with the backsheet uppermost, but the embodiment may just as easily be applied to the ear panels of a diaper. A sanitary towel 25, generally elongate in shape having opposing longitudinal sides 26, 27, and opposing transverse sides 28, 29. The backsheet is provided with first 30, 32 and second 31, 33 mechanical fastening means, the first 30, 32 mechanical fastening means having a width $w_1$ and the second mechanical fastening means 31, 33 having a width $w_2$, and being separated by a separation distance $d_1$. In all other respects, the first 30, 32 and second 31, 33 mechanical fastening means and the separation distances $d_1$ are the same as described with respect to the first and second embodiments of the present invention described above. In order to secure the hygiene article to a wearer's clothing, the mechanical fastening means engage with the inner side of the gusset of a wearer's underwear.

In both the third and fourth embodiments of the present invention, the mechanical fastening means are positioned so as to be perpendicular to the direction of removal of the hygiene article, taking advantage of the same force application and perception effects as described above in connection with the first and second embodiments of the present invention. For example, in the fourth embodiment of the present invention it is intended that the hygiene article is removed by peeling away from a garment starting at the upper edge (the transverse side 28) of the article. However, if it is more desirable for the user to be able to peel the hygiene article away from a garment by removing one of the longitudinal edges 26, 27 first, the mechanical fastening means 30, 31, 32, 33 would be positioned parallel to the chosen edge such that the first mechanical fastening means 30, 32 is always removed from the garment before the second mechanical fastening means 31, 33. Similarly, although FIG. 6 shows the arrangement of first 30, 32 and second 31, 33 mechanical fastening means as being identical in both positions on the sanitary towel, it may be desirable for the arrangements to be positioned as mirror images of each with the line of reflection passing horizontally across the centre of the sanitary towel. This would cause both of the second mechanical fastening means 31, 33 to lie nearest to each other, and for both first mechanical fastening means 30, 32 to lie adjacent the opposing transverse sides 28, 29.

The concept of using additional mechanical fastening means, such as the third and fourth mechanical fastening means described above in relation to the second embodiment of the present invention can also be extended to the third and fourth embodiments in a similar manner. For example, a third mechanical fastening means having a width $w_3$, separated from the second mechanical fastening means by a separation distance of $d_2$, may be provided either on the backsheet or on a wing portion. A fourth mechanical fastening means having a width $w_4$, separated from the third mechanical fastening means by a separation distance $d_3$ may be provided.

The invention claimed is:

1. Hygiene article closure tab, comprising:
    a backing layer having a manufacturer end and a user end, the user end carrying at least one mechanical fastening means and a fingerlift portion, the fingerlift portion being free from any fastening means;
    a first mechanical fastening means carried on the backing layer in the user end, the first mechanical fastening means positioned between the manufacturer end and the fingerlift portion, the first mechanical fastening means having a width $w_1$; and
    a second mechanical fastening means carried on the backing layer in the user end, the second mechanical fastening means positioned between the manufacturer end and the first mechanical fastening means, the second mechanical fastening means having a width $w_2$ and separated from the first mechanical fastening means by a separation distance $d_1$;
    wherein the width $w_1$ of the first mechanical fastening means is greater than the separation distance $d_1$ and the width $w_2$ of the second mechanical fastening means is greater than the width $w_1$ of the first mechanical fastening means; and wherein the separation distance $d_1$ is in the range of 0.2 to 1.2 mm.

2. The closure tab of claim 1, wherein the first and second mechanical fastening means comprise hook, stem or cup-shaped fasteners.

3. The closure tab of claim 1, wherein the first mechanical fastening means comprises fasteners optimised to resist peel force and the second mechanical fastening means comprises fasteners optimised to resist shear force.

4. The closure tab of claim 1, wherein the sum of the widths $w_1$ of the first mechanical fastening means and $w_2$ of the second mechanical fastening means is in the range 7 to 22 mm.

5. The closure tab of claim 1, further comprising a third mechanical fastening means carried on the backing layer in the user end, the third mechanical fastening means positioned between the manufacturer end and the second mechanical fastening means, the third mechanical fastening means having a width $w_3$ and separated from the second mechanical fastening means by a separation distance $d_2$.

6. The closure tab of claim 5, wherein the width $w_3$ of the third mechanical fastening means is equal to the width $w_2$ of the second mechanical fastening means.

7. The closure tab of claim 5, wherein the width $w_3$ of the third mechanical fastening means is not equal to the width $w_2$ of the second mechanical fastening means.

8. The closure tab of claim 5, wherein the separation distance $d_1$ between the first and second mechanical fastening means is equal to the separation distance $d_2$ between the second and third mechanical fastening means.

9. The closure tab of claim 5, further comprising a fourth mechanical fastening means carried on the backing layer in the user end, the fourth mechanical fastening means positioned between the manufacturer end and the third mechanical fastening means, the fourth mechanical fastening means having a width $w_4$ and separated from the third mechanical fastening means by a separation distance $d_3$.

10. The closure tab of claim 1, wherein the backing layer comprises a non-woven material layer and an adhesive layer.

11. The closure tab of claim 1, wherein the backing layer is formed by the backsheet material of a hygiene article.

12. The closure tab of claim 1, wherein the backing layer laterally disposed between the first mechanical fastening means and the second mechanical fastening means along separation distance $d_1$ is free from any fastening means.

13. The closure tab of claim 1, wherein a ratio of the separation distance $d_1$ to the sum of the widths of the first and second mechanical fastening means $w_1$ and $w_2$ is between 1:7 and 1:44.

14. The closure tab of claim 1, wherein a ratio of the separation distance $d_1$ and the width of the second mechanical fastening means $w_2$ is between 1:5 and 1:36.

15. The closure tab of claim 14, wherein a ratio of the width of the first mechanical means $w_1$ and the second mechanical means $w_2$ is less than 1:1 and greater than 1:18.

* * * * *